United States Patent
Anissian

(10) Patent No.: US 9,974,582 B1
(45) Date of Patent: May 22, 2018

(54) ORTHOPEDIC SURGICAL IMPLANTS AND METHODS

(71) Applicant: Lucas Anissian, Shreveport, LA (US)

(72) Inventor: Lucas Anissian, Shreveport, LA (US)

(*) Notice: Subject to any disclaimer, the term of this patent is extended or adjusted under 35 U.S.C. 154(b) by 567 days.

(21) Appl. No.: 14/632,476

(22) Filed: Feb. 26, 2015

(51) Int. Cl.
- *A61B 17/88* (2006.01)
- *A61B 17/74* (2006.01)
- *A61B 17/80* (2006.01)
- *A61B 17/56* (2006.01)
- *A61B 17/68* (2006.01)

(52) U.S. Cl.
CPC ........ *A61B 17/746* (2013.01); *A61B 17/8014* (2013.01); *A61B 2017/564* (2013.01); *A61B 2017/681* (2013.01)

(58) Field of Classification Search
None
See application file for complete search history.

(56) References Cited

U.S. PATENT DOCUMENTS

| | | | |
|---|---|---|---|
| 3,489,143 A | 1/1970 | Halloran | |
| 4,791,918 A * | 12/1988 | Von Hasselbach | A61B 17/746 606/286 |
| 5,356,410 A * | 10/1994 | Pennig | A61B 17/744 606/281 |
| 5,871,485 A | 2/1999 | Rao et al. | |
| 5,976,139 A | 11/1999 | Bramlet | |
| 8,137,350 B2 | 3/2012 | Nakamura | |
| 8,157,803 B1 | 4/2012 | Zirkle, Jr. et al. | |
| 8,398,636 B2 | 3/2013 | Simon et al. | |
| 2010/0174285 A1 | 7/2010 | Probe | |
| 2013/0317502 A1 | 11/2013 | Overes | |

* cited by examiner

*Primary Examiner* — Sameh Boles
(74) *Attorney, Agent, or Firm* — R. Keith Harrison

(57) ABSTRACT

Orthopedic surgical implant methods include placing an implant plate against a lateral greater trochanteric surface of a femur; installing at least one proximal compression fastener through the implant plate and through a greater trochanter and one of a fractured bone, a pretrochanteric neck fracture and a femoral neck fracture and into a femoral head of the femur, respectively; and installing at least one distal tension fastener through the implant plate and through a portion of a diaphysis of the femur and through the fractured femoral neck and into the femoral head of the femur, respectively, the at least one distal tension fastener intersecting the at least one proximal compression fastener in the femoral head. Orthopedic surgical implants are also disclosed.

15 Claims, 6 Drawing Sheets

ORTHOPEDIC SURGICAL IMPLANTS AND METHODS

FIELD

Illustrative embodiments of the disclosure generally relate to orthopedic surgical implants and methods for treating broken or fractured bones in orthopedic patients. More particularly, illustrative embodiments of the disclosure relate to orthopedic surgical implants and methods which are suitable for repair of a fractured femoral neck and pertrochanteric fractures.

SUMMARY

Illustrative embodiments of the disclosure are generally directed to orthopedic surgical implant methods. An illustrative embodiment of the orthopedic surgical implant methods includes placing an implant plate against a lateral greater trochanteric surface of a femur; installing at least one proximal compression fastener through the implant plate and through a greater trochanter and one of a fractured bone, a pretrochanteric neck fracture and a femoral neck fracture and into a femoral head of the femur, respectively; and installing at least one distal tension fastener through the implant plate and through a portion of a diaphysis of the femur and through the fractured femoral neck and into the femoral head of the femur, respectively, the at least one distal tension fastener intersecting the at least one proximal compression fastener in the femoral head.

Illustrative embodiments of the disclosure are further generally directed to orthopedic surgical implants. An illustrative embodiment of the orthopedic surgical implants include an implant plate including a proximal plate segment having a generally concave proximal bone engaging portion; a middle plate segment extending from the proximal plate segment, the middle plate segment having a generally convex middle bone engaging portion; a distal plate segment extending from the middle plate segment, the distal plate segment having a distal bone engaging portion; at least one proximal fastener opening in the proximal plate segment of the implant plate; and at least one distal fastener opening in the distal plate segment of the implant plate; at least one proximal compression fastener extending through the at least one proximal fastener opening; and at least one distal tension fastener extending through the at least one distal fastener opening.

BRIEF DESCRIPTION OF THE DRAWINGS

Illustrative embodiments of the disclosure will now be described, by way of example, with reference to the accompanying drawings, in which.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable users skilled in the art to practice the disclosure and are not intended to limit the scope of the claims. Moreover, the illustrative embodiments described herein are not exhaustive and embodiments or implementations other than those which are described herein and which fall within the scope of the appended claims are possible. Furthermore, there is no intention to be bound by any expressed or implied theory presented in the preceding technical field, background, brief summary or the following detailed description. As used herein, the terms "anterior", "posterior", "lateral" and "medial" generally refer to the front, the back, the position which is further from the midline and the position which is nearer to the midline, respectively, of a surgical patient. The terms "proximal" and "distal" generally indicate positions which are closer to and further from, respectively, the femoral head of a femur of the patient.

Figure 1:
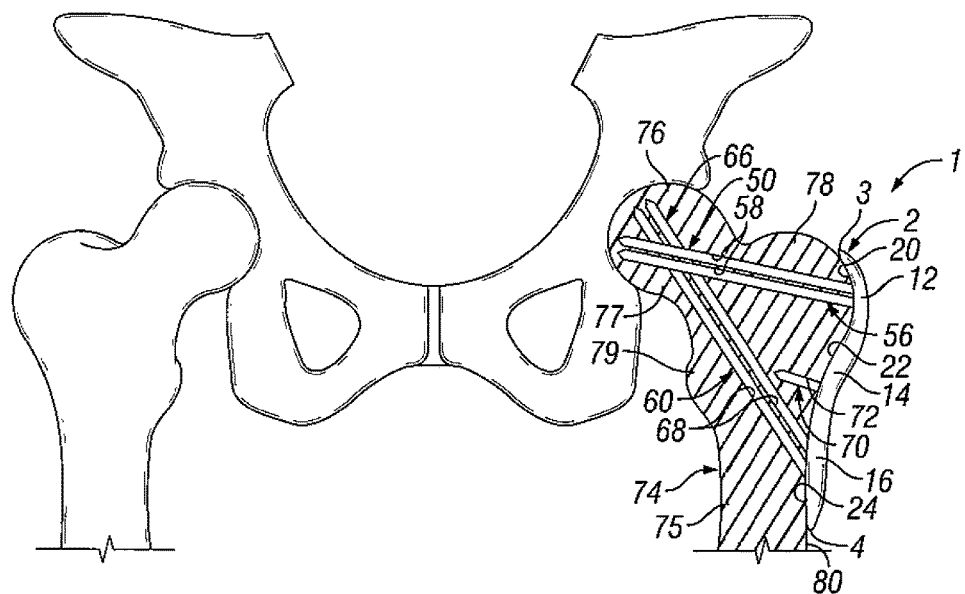
FIG. 1 is a front view of a human pelvis and an illustrative embodiment of the orthopedic surgical implants installed in a femur (illustrated in section) connected to the pelvis in typical repair of a perthrochanteric or femoral neck fracture.
Figure 7:
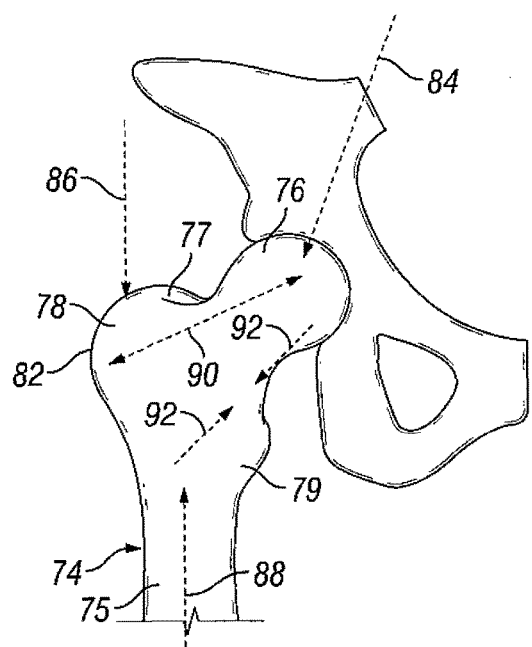
FIG. 7 is a schematic diagram illustrating tension and compression forces which an installed orthopedic surgical implant applies to the repaired femoral neck and a body weight force, an abduction force and a ground force applied to the pelvis in the standing or walking patient.

Referring initially to FIGS. 1-10 of the drawings, an illustrative embodiment of the orthopedic surgical implant is generally indicated by reference numeral 1. As illustrated in FIG. 1 and will be hereinafter described, the orthopedic surgical implant 1 is suitable for repair of a fractured bone, ideally a pertrochanteric fracture, and/or a femoral neck fracture 77 in a femur 74 of a patient. The orthopedic surgical implant 1 includes an implant plate 2 which engages the lateral greater trochanteric surface 82 (FIG. 5) and the lateral diaphyseal surface 80 of the femur 74. At least one proximal compression fastener 50, 56 is extended through at least one proximal fastener opening 30, 32 (FIGS. 3 and 4, respectively) in the implant plate 2 and typically threaded in at least one compression fastener opening 58 (FIG. 1) which extends through the greater trochanter 78 and the femoral neck 77, respectively, and terminates in the femoral head 76 of the femur 74. As will be hereinafter described, engagement of compression heads 53 (FIG. 5) on the proximal compression fasteners 50, 56 with, against or into the implant plate 2 generates compression forces 92 (FIG. 7) at the fracture site in an upper part of the femoral neck 77 to neutralize tension forces 90 on superior part of the femoral neck 77. At least one distal tension fastener 60, 66 is extended through at least one distal fastener opening 34, 36 (FIGS. 3 and 4, respectively) in the implant plate 2 and typically threaded in at least one tension fastener opening 68 (FIG. 1) which extends through a portion of the diaphysis 75 and the femoral neck 77, respectively, and terminates in the femoral head 76. At least one insertion handle opening fastener 70 (FIG. 1) may be extended through an insertion handle opening 40 (FIG. 3) in the implant plate 2 and threaded into a fastener opening 72 (FIG. 1) which extends into the femur 74 typically between the diaphysis 75 and the greater trochanter 78. Accordingly, the implant plate 2, the proximal compression fastener or fasteners 50, 56 and the distal tension fastener or fasteners 60, 66 stabilize the fractured femoral neck 77 for healing of a fracture in the femoral neck 77. Additionally, as illustrated in FIG. 7 and will be hereinafter described, the proximal compression fastener or fasteners 50, 56 resist biomechanical tension forces 90 in the proximal portion of the fractured femoral neck 77, whereas the distal tension fastener or fasteners 60, 66 resist biomechanical compression forces 92 in the distal portion of the fractured femoral neck 77, in the femur 74 of the standing or walking patient. The implant plate 2, the proximal compression fastener or fasteners 50, 56, the distal tension fastener or fasteners 60, 66 and the insertion handle opening fastener 70 may be fabricated of a metal alloy such as titanium alloy, for example and without limitation, and/or any other ASTM pharmaceutical grade material which is suitable for the purpose. The thickness and length of the implant plate 2, the proximal compression fasteners 50, 56 and the distal tension fasteners 60, 66 may vary to match the patient's anatomy.

Figure 2:
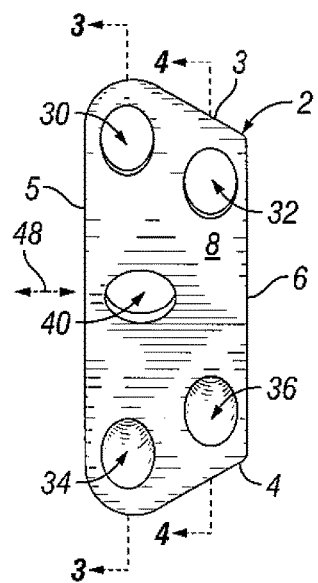
FIG. 2 is a side view of a typical implant plate of an illustrative embodiment of the orthopedic surgical implants.
Figure 3:
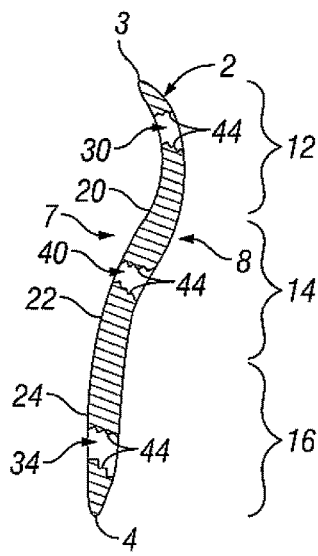
FIG. 3 is a longitudinal sectional view, taken along section lines 3-3 in FIG. 2, of an anterior portion of the implant plate.
Figure 4:
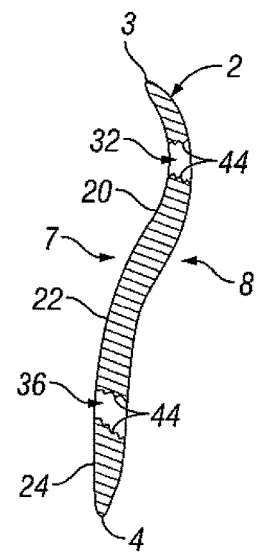
FIG. 4 is a longitudinal sectional view, taken along section lines 4-4 in FIG. 2, of a posterior portion of the implant plate.

As illustrated in FIGS. 2-4, the implant plate 2 of the orthopedic surgical implant 1 may be generally elongated with a proximal plate edge 3, a distal plate edge 4, an anterior plate edge 5, a posterior plate edge 6, a medial plate surface 7 and a lateral plate surface 8. In some embodiments, the posterior plate edge 6 may be generally parallel to the anterior plate edge 5. The proximal plate edge 3 and the distal plate edge 4 may angle inwardly toward each other from the proximal plate edge 5 to the shorter distal plate edge 6. In other embodiments, the implant plate 2 may have alternative shapes which are consistent with the functional requirements of the implant plate 2 in the orthopedic surgical implant 1.

The implant plate 2 may be contoured to conform to the lateral greater trochanteric surface 82 and the lateral diaphyseal surface 80 (FIG. 5) of the femur 74. Accordingly, as illustrated in FIGS. 3 and 4, the implant plate 2 may include a proximal plate segment 12, a middle plate segment 14 which extends from the proximal plate segment 12 and a distal plate segment 16 which extends from the middle plate segment 14. The proximal plate segment 12 may have a proximal bone engaging portion 20 which is generally concave in cross-section at the medial plate surface 7. The middle plate segment 14 may have a middle bone engaging portion 22 which is generally convex in cross-section at the medial plate surface 7. The distal plate segment 16 may have a distal bone engaging portion 24 which is generally straight or planar in cross-section at the medial plate surface 7. Thus, in installation of the orthopedic surgical implant 1, which will be hereinafter described, the generally concave proximal bone engaging portion 20 and the generally convex middle bone engaging portion 22 may engage the generally convex and concave portions, respectively, of the lateral greater trochanteric surface 82 on the greater trochanter 78 of the femur 74. The distal bone engaging portion 24 may engage the lateral diaphyseal surface 80 on the diaphysis 75 of the femur 74.

As illustrated in FIGS. 3 and 4, at least one proximal fastener opening 30, 32 may extend through the proximal plate segment 12 of the implant plate 2. In some embodiments, an anterior proximal fastener opening 30 (FIGS. 2 and 3) and a posterior proximal fastener opening 32 (FIGS. 2 and 4) may extend through the anterior and posterior portions, respectively, of the proximal plate segment 12. At least one distal fastener opening 34, 36 may extend through the distal plate segment 16 of the implant plate 2. In some embodiments, an anterior distal fastener opening 34 (FIGS. 2 and 3) and a posterior distal fastener opening 36 (FIGS. 2 and 4) may extend through the anterior and posterior portions, respectively, of the distal plate segment 16. As illustrated in FIG. 2, each of the anterior proximal fastener opening 30, the posterior proximal fastener opening 32, the anterior distal fastener opening 34 and the posterior distal fastener opening 36 may be generally oval or elliptical and elongated along a longitudinal axis of the implant plate 2 to facilitate multi-positional capability or selected degrees of freedom for insertion of the proximal compression fasteners 50, 56 and the distal tension fasteners 60, 66 in installation of the orthopedic surgical implant 1, which will be hereinafter described. As further illustrated in FIGS. 3 and 4, each anterior proximal fastener opening 30, posterior proximal fastener opening 32, anterior distal fastener opening 34 and posterior distal fastener opening 36 may have interior fastener opening threads 44 for purposes which will be hereinafter described. As illustrated in FIG. 2, in some embodiments, the anterior proximal fastener opening 30 and the posterior proximal fastener opening 32 may be offset to each other along an axis 48 which is transverse to a longitudinal axis of the implant plate 2 and the anterior distal fastener opening 34 and the posterior distal fastener opening 36 may be offset to each other along the axis 48 which is transverse to the longitudinal axis of the implant plate 2. In some embodiments, the anterior proximal fastener opening 30, the anterior distal fastener opening 32, the anterior distal fastener opening 34 and the posterior distal fastener opening 36 may be conventional round, angled, fully-threaded and/or partially-threaded openings with threads only on two sides of each opening, ideally longitudinally to allow adjustment of the level of the insertion of the proximal compression fasteners 50, 56 and the distal tension fasteners 60, 66 threaded into the respective openings in installation of the orthopedic surgical implant 1.

As illustrated in FIGS. 2 and 3, at least one insertion handle opening 40 extends through the implant plate 2. In some embodiments, the insertion handle opening 40 may extend through the middle bone engaging portion 22 of the implant plate 2, as illustrated in FIG. 3. The insertion handle opening 40 may be semi-threaded or completely threaded with interior fastener opening threads 44 (FIG. 3) which match the companion threads on an insertion handle (not illustrated) for purposes which will be hereinafter described.

Figure 5:
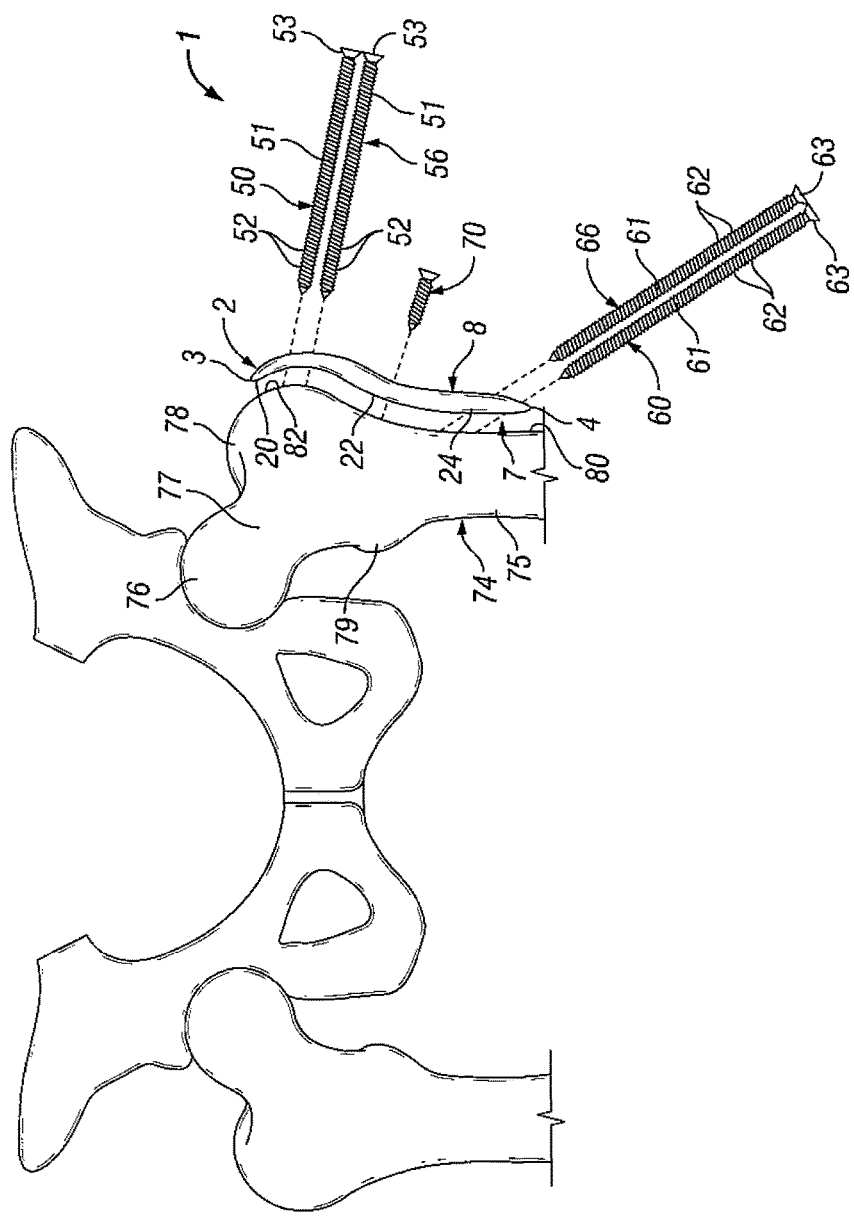
FIG. 5 is a front view of a human pelvis illustrating typical installation of an illustrative embodiment of the orthopedic surgical implants (illustrated in exploded view) in typical repair of a fractured femoral neck.
Figure 6:
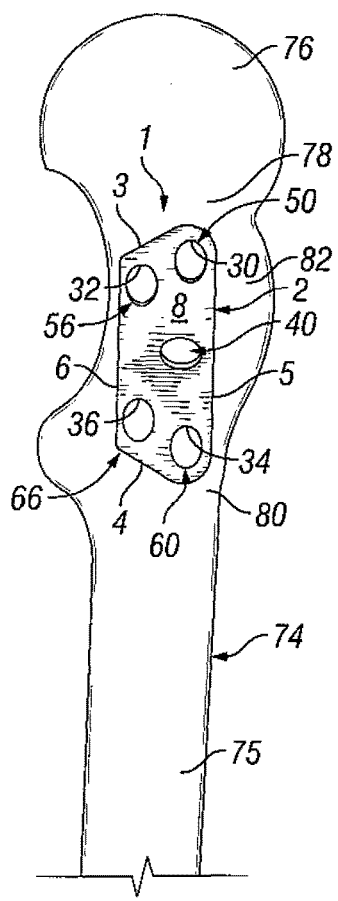
FIG. 6 is a side view of an upper portion of a femur with an illustrative embodiment of the orthopedic surgical implants installed on the femur in typical repair of a fractured femoral neck.
Figure 8:
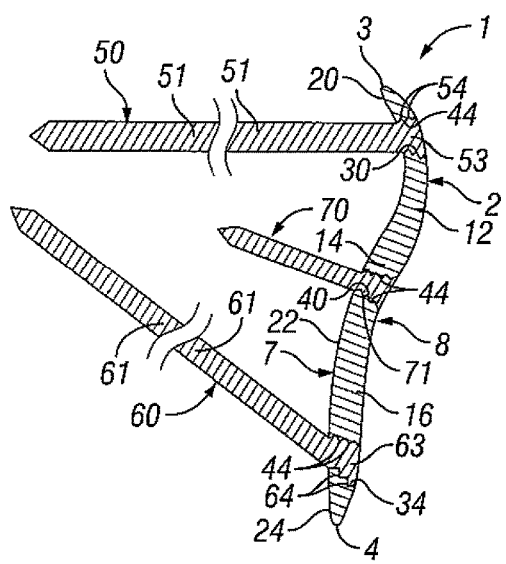
FIG. 8 is a longitudinal sectional view of the anterior portion of the implant plate, taken along section lines 3-3 in FIG. 2, with an anterior proximal compression fastener, an insertion handle opening fastener and an anterior distal tension fastener extending through an anterior proximal fastener opening, an insertion handle opening and an anterior distal fastener opening, respectively, in the implant plate in an illustrative embodiment off the installed orthopedic surgical implants.
Figure 9:
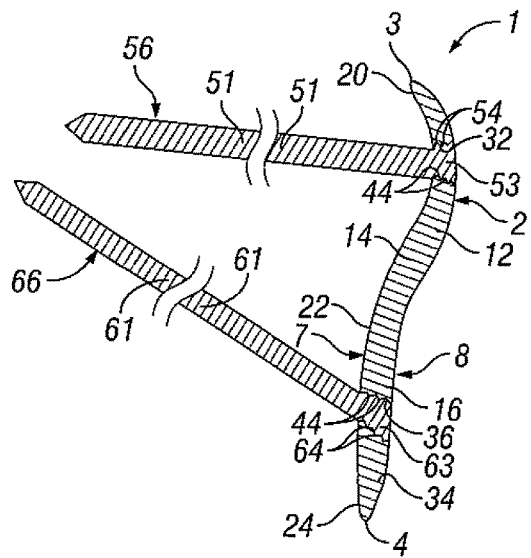
FIG. 9 is a longitudinal sectional view of the posterior portion of the implant plate, taken along section lines 4-4 in FIG. 2, with a posterior proximal compression fastener and a posterior distal tension fastener extending through a posterior proximal fastener opening and a posterior distal fastener opening, respectively, in the implant plate in an illustrative embodiment of the installed orthopedic surgical implants.

As illustrated in FIGS. 8 and 9, in typical installation of the orthopedic surgical implant 1, which will be hereinafter described, the anterior proximal compression fastener 50 and the posterior proximal compression fastener 56 are extended through the anterior proximal fastener opening 30 and posterior proximal fastener opening 32, respectively, in the implant plate 2 and threaded into the respective registering compression fastener openings 58 (FIG. 1) in the femur 74. Likewise, the anterior distal tension fastener 60 and the posterior distal tension fastener 66 are extended through the anterior distal fastener opening 34 and the posterior distal fastener opening 36, respectively, and threaded into the respective registering tension fastener openings 68 (FIG. 1) in the femur 74. Each of the anterior proximal compression fastener 50 and the posterior proximal compression fastener 56 may be a standard or conventional orthopedic compression screw known by those skilled in the art. As illustrated in FIG. 5, the anterior proximal compression fastener 50 and the posterior proximal compression fastener 56 may each include an elongated compression fastener shaft 51 which may be partially-threaded or fully-threaded with shaft threads 52 and a compression fastener head 53 on the compression fastener shaft 51. As illustrated in FIGS. 8 and 9, in some embodiments, the compression fastener head 53 may include head threads 54 which may at least partially engage the companion fastener opening threads 44 in the corresponding anterior proximal fastener opening 30 and posterior proximal fastener opening 32.

Each of the anterior distal tension fastener 60 and the posterior distal tension fastener 66 may be a standard or conventional orthopedic locking screw known by those skilled in the art. As further illustrated in FIG. 5, the anterior distal tension fastener 60 and the posterior distal tension fastener 66 may each include an elongated tension fastener shaft 61 having shaft threads 62 and a tension fastener head 63 on the tension fastener shaft 61. As illustrated in FIGS. 8 and 9, in some embodiments, the tension fastener head 63 may include head threads 64 which may at least partially engage the companion fastener opening threads 44 in the corresponding anterior distal fastener opening 34 and posterior distal fastener opening 36.

In typical application, the orthopedic surgical implant 1 is installed in the femur 74 of a patient to stabilize a fractured femoral neck 77 on the femur 74 in repair of the femoral neck 74. Accordingly, the upper or proximal portion of the femur 74, including the upper or lateral portion of the diaphysis 75, greater trochanter 78, lesser trochanter 79, femoral neck 77 and femoral head 76, is surgically exposed typically using standard or conventional orthopedic surgical techniques. Next, the implant plate 2 may be placed into contact with the femur 74 with the proximal bone engaging portion 20 on the proximal plate segment 12 and the middle bone engaging portion 22 on the middle plate segment 14 engaging the lateral greater trochanteric surface 82 (FIG. 5) of the greater trochanter 78 and the distal bone engaging portion 24 on the distal plate segment 16 engaging the lateral diaphyseal surface 80 of the femur 74. This may be accomplished by inserting and threading an insertion handle (not illustrated) in the insertion handle opening 40 of the implant plate 2 and holding the implant plate 2 against the femur 74 using the insertion handle. Drill guides (not illustrated) may be placed in optimal positions across the fracture in the femoral neck 77 such as by using fluoroscopic images in the conventional manner. In some embodiments, the anterior proximal fastener opening 30 and the posterior proximal fastener opening 32 may be dented (not illustrated) to accept the drill guides. The drill guide angle may vary between about 0±15 degrees.

The compression fastener openings 58 (FIG. 1) may next be drilled through the greater trochanter 78 and the femoral neck 77, respectively, and into the femoral head 76 using conventional surgical drilling techniques. The anterior proximal compression fastener 50 and the posterior proximal compression fastener 56 may then be inserted through the anterior proximal fastener opening 30 and the posterior proximal fastener opening 32, respectively, in the implant plate 2 and threaded into the respective registering compression fastener openings 58. As illustrated in FIGS. 8 and 9, in some applications, the head threads 54 on the compression fastener heads 53 of the respective anterior proximal compression fastener 50 and posterior proximal compression fastener 56 may at least partially engage the companion fastener opening threads 44 in the anterior proximal fastener opening 30 and posterior proximal fastener opening 32, respectively.

After installation of the anterior proximal compression fastener 50 and the posterior proximal compression fastener 56 is completed, the insertion handle (not illustrated) may be unthreaded and removed from the insertion handle opening 40 in the implant plate 2. The fastener opening 72 (FIG. 1) may be drilled in the femur 74, and the insertion handle opening fastener 70 may be inserted through the insertion handle opening 40 and threaded into the registering fastener opening 72 to additionally secure the implant plate 2 on the femur 74. In some embodiments, head threads 71 (FIG. 8) may be provided on the fastener head of the insertion handle opening fastener 70 to threadably engage the companion fastener opening threads 44 in the insertion handle opening 40. In some applications, prior to installation of the handle opening fastener 70, an injection device (not illustrated) may be inserted through the insertion handle opening 40 to facilitate injection of a bone density increasing composition known by those skilled in the art (not illustrated) to enhance the bone density of that portion of the femur 74. After application of the composition, the insertion handle opening 40 may be drilled and the handle opening fastener 70 installed typically as was heretofore described.

The tension fastener openings 68 may next be drilled through the upper or proximal portion of the diaphysis 75 adjacent to the lesser trochanter 79 and through the femoral neck 77, respectively, and into the femoral head 76 using conventional surgical drilling techniques. The anterior distal tension fastener 60 and the posterior distal tension fastener 66 may then be inserted through the anterior distal fastener opening 34 and the posterior distal fastener opening 36, respectively, in the implant plate 2 and threaded into the respective registering tension fastener openings 68. As illustrated in FIGS. 8 and 9, in some applications, the head threads 64 on the tension fastener heads 63 of the respective anterior distal tension fastener 60 and posterior distal tension fastener 66 may at least partially engage the companion fastener opening threads 44 in the anterior distal fastener opening 34 and posterior distal fastener opening 36, respectively.

Figure 10:
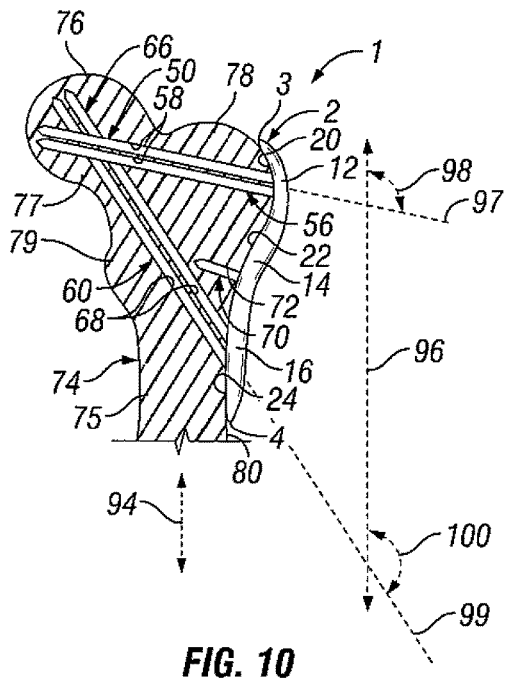
FIG. 10 is a sectional view of the upper portion of the femur with the illustrative orthopedic surgical implant installed in the femur, more particularly illustrating typical angles of the anterior and posterior proximal compression fasteners and anterior and posterior distal tension fasteners relative to an axis which is parallel to a longitudinal femur axis of the femur in an illustrative embodiment of the installed orthopedic surgical implants.

As illustrated in FIG. 10, a compression fastener axis 97 of the anterior proximal compression fastener 50 and the posterior proximal compression fastener 56 may be installed at a compression fastener angle 98 relative to an axis 96 which is parallel to a longitudinal femoral axis 94 of the femur 74. In some applications, the compression fastener angle 98 may be from about 80 degrees to about 100 degrees. A tension fastener axis 99 of the anterior distal tension fastener 60 and the posterior distal tension fastener 66 may be installed at a tension fastener angle 100 relative to the axis 96. In some applications, the tension fastener angle 100 may be from about 120 degrees to about 150 degrees. Thus, the anterior distal tension fastener 60 and the posterior distal tension fastener 66 may intersect the anterior proximal compression fastener 50 and the posterior proximal compression fastener 56 in a single plane in the femoral head 76, forming a diamond shape on anterior fluoroscopic view of the femoral head 76. The compression fastener angle 98 may enable the anterior proximal compression fastener 50 and posterior proximal compression fastener 56 to resist the biomechanical tension force 90 (FIG. 7) on the femoral neck 77 of the femur 74. Likewise, the tension fastener angle 100 may enable the anterior distal tension fastener 60 and posterior distal tension fastener 66 to resist the biomechanical compression force 92 (FIG. 7) on the femoral neck 77 of the femur 74.

After the orthopedic surgical implant 1 is installed, the surgical site is closed typically in the conventional manner. As illustrated in FIG. 7, as the recovered or recovering patient stands erect, the patient's body weight 84 and an abduction force 86 are applied against the femoral head 76 and the greater trochanter 78, respectively, of the repaired femur 74. The ground force 88 exerts upward pressure which counteracts the body weight 84 and the abduction force 86. A biomechanical tension force 90 is applied across the proximal portion of the repaired femoral neck 77, whereas a biomechanical compression force 92 is applied across the distal portion of the femoral neck 77. Accordingly, the proximal compression fastener or fasteners 50, 56 (FIG. 1) resist the biomechanical tension force 90 whereas the distal tension fastener or fasteners 60, 66 (FIG. 1) resist the biomechanical compression force 92. Consequently, the intersecting diamond orientation of the proximal compression fastener or fasteners 50, 56 and the distal tension fastener or fasteners 60, 66 may resist torque which is applied to the femoral neck 77 during walking of the patient. In contrast, conventional orthopedic surgical implants are typically incapable of resisting femoral neck torque, potentially resulting in shortening of the femoral neck and less-than-optimum distribution of biomechanical forces, potentially leading to limping and pain in the patient.

It will be appreciated by those skilled in the art that the insertion sites and angles of the anterior proximal compression fastener 50, the posterior proximal compression fastener 56, the anterior distal tension fastener 60 and the posterior distal tension fastener 66 of the orthopedic surgical implants and methods address the post-surgical biomechanical forces which are applied to the femur 74 including the tension force 90 and the compression force 92 (FIG. 7). The compression fastener angle 98 (FIG. 10), the tension fastener angle 100, the anterior proximal compression fastener 50, the posterior proximal compression fastener 56, the anterior distal tension fastener 60 and the posterior distal tension fastener 66 may be conventional and may each be selected according to its suitability to apply the biomechanical forces to the femur. For example, conventional compression screws which are routinely used in orthopedic surgical procedures can be used as the anterior proximal compression fastener 50 and the posterior proximal compression fastener 56 to resist the compression force 92 (FIG. 7) in the femoral neck 77. Conventional locking screws can be used as the anterior distal tension fastener 60 and the posterior distal tension fastener 66 to resist the tension forces 92 (FIG. 7) in the femoral neck 77.

Figure 11A:
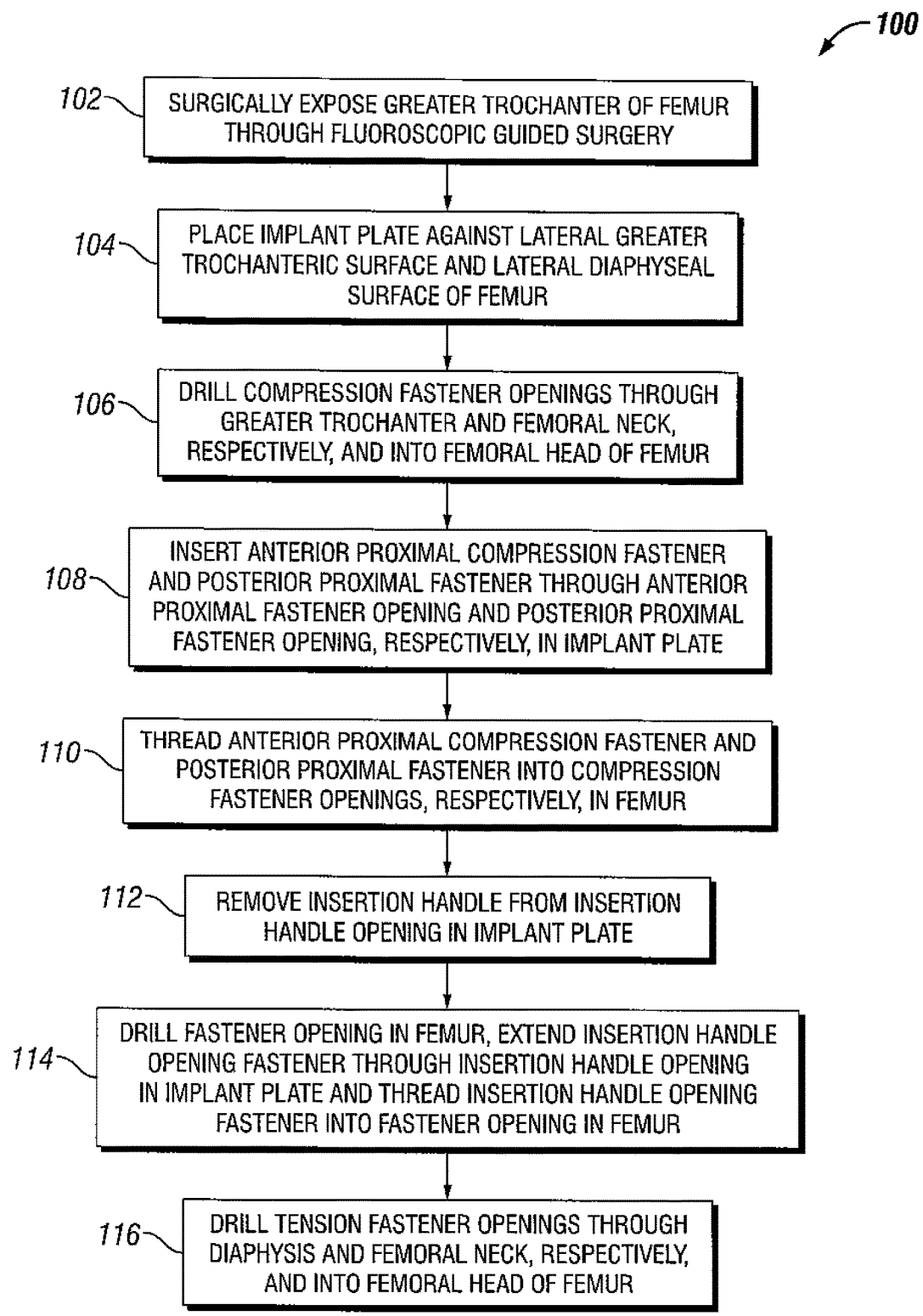
FIG. 11A is a flow diagram of an illustrative embodiment of the orthopedic surgical implant methods.
Figure 11B:
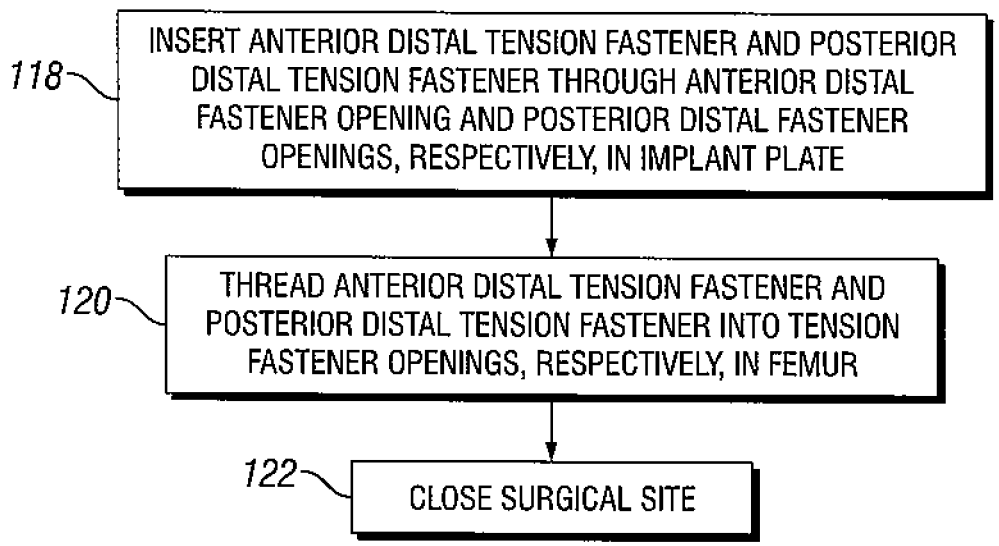
FIG. 11B is a continuation of the flow diagram illustrated in FIG. 11A.

Referring next to FIG. 11 of the drawings, an illustrative embodiment of the orthopedic surgical implant methods is generally indicated by reference numeral 100. At block 102, the greater trochanter of a femur of a patient is surgically exposed typically using fluoroscopic surgery. At block 104, an implant plate may be placed against the lateral greater trochanteric surface and the lateral diaphyseal surface of the femur. This may be accomplished by threading an insertion handle into an insertion handle opening in the implant plate and placing the implant plate against the lateral greater trochanteric surface and the lateral diaphyseal surface of the femur using the insertion handle. At block 106, compression fastener openings may be drilled through the greater trochanter and the fractured femoral neck, respectively, and into the femoral head of the femur. At block 108, an anterior proximal compression fastener and a posterior proximal compression fastener may be inserted through an anterior proximal fastener opening and a posterior proximal fastener opening, respectively, in the implant plate. At block 110, the anterior proximal compression fastener and the posterior proximal compression fastener may be threaded into the compression fastener openings, respectively, in the femur.

At block 112, the insertion handle may be removed from the insertion handle opening in the implant plate. At block 114, a fastener opening may be drilled in the femur. An insertion handle opening fastener may be inserted through the insertion handle opening in the implant plate and threaded into the fastener opening in the femur.

At block 116, tension fastener openings may be drilled through the diaphysis and the femoral neck, respectively, and into the femoral head of the femur. In some embodiments, the tension fastener openings may be conventional round, angled, fully-threaded and/or oblong openings with threads only on two sides of each opening, ideally longitudinally to allow adjustment of the level of the insertion of fasteners threaded into the openings. At block 118, an anterior distal tension fastener and a posterior distal tension fastener may be extended through an anterior distal fastener opening and a posterior distal fastener opening, respectively, in the implant plate. At block 120, the anterior distal tension fastener and the posterior distal tension fastener may be threaded into the tension fastener openings, respectively, in the femur. At block 122, the surgical site may be closed. The anterior distal tension fastener and the posterior distal tension fastener may intersect the anterior proximal compression fastener and the posterior proximal compression fastener in the femoral head and may form a diamond shape on anterior fluoroscopic view of the femoral head. A compression fastener angle of the anterior and posterior proximal compression fasteners may be from about 75 degrees to about 100 degrees. A tension fastener angle of the anterior and posterior distal tension fasteners may be from about 120 degrees to about 160 degrees.

While illustrative embodiments of the disclosure have been described above, it will be recognized and understood that various modifications can be made in the disclosure and the appended claims are intended to cover all such modifications which may fall within the spirit and scope of the disclosure.

What is claimed is:

1. An orthopedic surgical implant method, comprising:
   placing an implant plate against a lateral greater trochanteric surface of a femur, the implant plate generally elongated in shape with at least one proximal fastener opening and at least one distal fastener opening, the at least one proximal fastener opening and the at least one distal fastener opening generally oval or elliptical and elongated along a longitudinal axis of the implant plate;
   installing at least one proximal compression fastener through the at least one proximal fastener opening in the implant plate and through a greater trochanter and a fracture site at one of a fractured bone, a pretrochanteric neck fracture and a femoral neck fracture and into a femoral head of the femur, respectively, the at least one proximal compression fastener having a compression fastener head, engagement of the compression fastener head on the proximal compression fastener with, against or into the implant plate generates compression forces at the fracture site to neutralize tension forces in a superior part of the femoral neck; and
   installing at least one distal tension fastener through the at least one distal fastener opening in the implant plate and through a portion of a diaphysis of the femur and through the fracture site at the fractured femoral neck and into the femoral head of the femur, respectively, the at least one distal tension fastener intersecting in one plane, the at least one proximal compression fastener in the femoral head, the at least one distal tension fastener having a tension fastener head, engagement of the tension fastener head on the at least one distal tension fastener with, against or into the implant plate generates tension forces at the fracture site to neutralize compression forces in a distal portion of the fractured femoral neck.

2. The orthopedic surgical implant method of claim 1 further comprising installing an insertion handle opening fastener through the implant plate and into the femur.

3. The orthopedic surgical implant method of claim 1 wherein placing an implant plate against a lateral greater trochanteric surface of a femur comprises placing an implant plate having a proximal plate segment, a middle plate segment extending from the proximal plate segment and a distal plate segment extending from the middle plate segment against the femur, and wherein installing at least one proximal compression fastener through the at least one proximal fastener opening in the implant plate comprises installing at least one proximal compression fastener through the at least one proximal fastener opening in the proximal plate segment and installing at least one distal tension fastener through the at least one distal fastener opening in the implant plate comprises installing at least one distal tension fastener through the at least one distal fastener opening in the distal plate segment.

4. The orthopedic surgical implant method of claim 3 wherein placing an implant plate having a proximal plate segment, a middle plate segment extending from the proximal plate segment and a distal plate segment extending from the middle plate segment against the femur comprises placing an implant plate having a proximal plate segment with a generally convex proximal bone engaging portion against the lateral greater trochanteric surface of the femur, a middle plate segment with a generally convex middle bone engaging portion against the lateral greater trochanteric surface of the femur and a distal plate segment with a distal bone engaging portion against a lateral diaphyseal surface of the femur.

5. The orthopedic surgical implant method of claim 4 further comprising installing an insertion handle opening fastener through the middle plate segment of the implant plate and into the femur.

6. The orthopedic surgical implant method of claim 1 wherein the at least one proximal compression fastener is disposed at a compression fastener angle of from about 75 degrees to about 100 degrees relative to a longitudinal femoral axis of the femur.

7. The orthopedic surgical implant method of claim 1 wherein the at least one distal tension fastener is disposed at a tension fastener angle of from about 120 degrees to about 160 degrees relative to a longitudinal femoral axis of the femur.

8. The orthopedic surgical implant method of claim 1 wherein the at least one proximal compression fastener comprises an anterior proximal compression fastener and a posterior proximal compression fastener and the at least one distal tension fastener comprises an anterior distal tension fastener and a posterior distal tension fastener.

9. An orthopedic surgical implant method, comprising:
   placing an implant plate against a lateral greater trochanteric surface of a femur, the implant plate generally elongated and trapezoidal in shape and including:
   a proximal plate segment;
   an anterior proximal fastener opening and a posterior proximal fastener opening in the proximal plate segment, the anterior proximal fastener opening and the posterior proximal fastener opening generally oval or elliptical and elongated along a longitudinal axis of the implant plate;
   interior fastener opening threads in each of the anterior proximal fastener opening and the posterior proximal fastener opening;
   a middle plate segment extending from the proximal plate segment;
   a distal plate segment extending from the middle plate segment;
   an anterior distal fastener opening and a posterior distal fastener opening in the distal plate segment, the anterior distal fastener opening and the posterior distal fastener opening generally oval or elliptical and elongated along the longitudinal axis of the implant plate, the anterior proximal fastener opening and the posterior proximal fastener opening are offset to each other along an axis transverse to the implant plate and the anterior distal fastener opening and the posterior distal fastener opening are offset to each other along the axis transverse to the implant plate; and
   interior fastener opening threads in each of the anterior distal fastener opening and the posterior distal fastener opening;
   installing an anterior proximal compression fastener through the anterior proximal fastener opening in the implant plate and through a greater trochanter and a fracture site at a fractured femoral neck and into a femoral head of the femur, respectively;
   installing a posterior proximal compression fastener through the posterior proximal fastener opening in the implant plate and through the greater trochanter and the fracture site at the fractured femoral neck and into the femoral head of the femur, respectively, the anterior proximal compression fastener and the posterior proximal compression fastener each having a compression fastener head and head threads on the compression fastener head, engagement of the head threads on the compression fastener head of each of the anterior proximal compression fastener and the posterior proximal compression fastener with the interior fastener opening threads in the anterior proximal fastener opening and the posterior proximal fastener opening generates compression forces at the fracture site to neutralize tension forces in a superior part of the femoral neck;

installing an anterior distal tension fastener through the anterior distal fastener opening in the implant plate and through a portion of a diaphysis of the femur and through the fracture site at the fractured femoral neck and into the femoral head of the femur, respectively; and installing a posterior distal tension fastener through the posterior distal fastener opening in the implant plate and through the portion of the diaphysis of the femur and through the fractured femoral neck and into the femoral head of the femur, respectively, the anterior distal tension fastener and the posterior distal tension fastener intersecting the anterior proximal compression fastener and the posterior proximal compression fastener in the femoral head, the anterior distal tension fastener and the posterior distal tension fastener each having a tension fastener head and head threads on the tension fastener head, engagement of the head threads on the tension fastener head of each of the anterior distal tension fastener and the posterior distal tension fastener with the interior fastener opening threads in the anterior distal fastener opening and the posterior distal fastener opening generates tension forces at the fracture site to neutralize compression forces in a distal portion of the fractured femoral neck.

10. The orthopedic surgical implant method of claim 9 wherein placing an implant plate against a lateral greater trochanteric surface of a femur comprises inserting and threading an insertion handle in an insertion handle opening in the implant plate and holding the implant plate against the femur using the insertion handle, and further comprising removing the insertion handle from the insertion handle opening and installing an insertion handle opening fastener through the insertion handle opening in the implant plate and into the femur after installing the anterior proximal compression fastener and the posterior proximal compression fastener.

11. The orthopedic surgical implant method of claim 9 wherein placing an implant plate having a proximal plate segment, a middle plate segment extending from the proximal plate segment and a distal plate segment extending from the middle plate segment against the femur comprises placing an implant plate having a proximal plate segment with a generally convex proximal bone engaging portion against the lateral greater trochanteric surface of the femur, a middle plate segment with a generally convex middle bone engaging portion against the lateral greater trochanteric surface of the femur and a distal plate segment with a distal bone engaging portion against a lateral diaphyseal surface of the femur.

12. The orthopedic surgical implant method of claim 11 further comprising installing an insertion handle opening fastener through the middle plate segment of the implant plate and into the femur.

13. The orthopedic surgical implant method of claim 9 wherein each of the anterior proximal compression fastener and the posterior proximal compression fastener is disposed at a compression fastener angle of from about 75 degrees to about 100 degrees relative to a longitudinal femoral axis of the femur.

14. The orthopedic surgical implant method of claim 9 wherein each of the anterior distal tension fastener and the posterior distal tension fastener is disposed at a tension fastener angle of from about 120 degrees to about 160 degrees relative to a longitudinal femoral axis of the femur.

15. The orthopedic surgical implant method of claim 9 wherein placing an implant plate against a lateral greater trochanteric surface of a femur comprises placing an implant plate including an anterior proximal fastener opening and a posterior proximal fastener opening in the proximal plate segment and an anterior distal fastener opening and a posterior distal fastener opening in the distal plate segment against the lateral greater trochanteric surface of a femur, with the anterior proximal fastener opening, the posterior proximal fastener opening, the anterior distal fastener opening and the posterior distal fastener opening each having at least one of the following configurations: angled, fully-threaded, and partially-threaded with threads limited to two sides of each opening.

* * * * *